United States Patent

Naef et al.

[11] Patent Number: 5,760,277
[45] Date of Patent: Jun. 2, 1998

[54] PROCESS FOR THE MANUFACTURE OF UNSATURATED CYCLOALIPHATIC KETONES

[75] Inventors: Ferdinand Naef, Carouge; René Decorzant, Onex, both of Switzerland

[73] Assignee: Firmenich SA, Geneva, Switzerland

[21] Appl. No.: 765,801

[22] PCT Filed: May 28, 1996

[86] PCT No.: PCT/IB96/00499

§ 371 Date: Jan. 15, 1997

§ 102(e) Date: Jan. 15, 1997

[87] PCT Pub. No.: WO96/41789

PCT Pub. Date: Dec. 27, 1996

[30] Foreign Application Priority Data

Jun. 8, 1995 [CH] Switzerland ............... 1676/95

[51] Int. Cl.[6] ............................... C07C 67/32
[52] U.S. Cl. ................. 560/121; 568/390; 568/379
[58] Field of Search ................... 568/390, 379; 560/121

[56] References Cited

U.S. PATENT DOCUMENTS

| | | | |
|---|---|---|---|
| 2,069,861 | 2/1937 | St. Pfau | 568/390 |
| 2,088,021 | 7/1937 | Wickert et al. | 568/390 |
| 2,957,027 | 10/1960 | Beets et al. | 568/390 |
| 3,158,644 | 11/1964 | Demole | 568/390 |

FOREIGN PATENT DOCUMENTS 21 62 822  7/1972  Germany.

OTHER PUBLICATIONS

E. Piers et al., "Five-membered ring spiro-annulation via thermal rearrangement of enol silyl ethers of 2-(cyclopropylmethylene)cycloalkanones. A formal total synthesis of some spirovetivane-type sesquiterpenoids", *Can. J. Chem.*, vol. 61 (1983) pp. 288–297.

E. Demole, "The Fragrance of Jasmine", *Fragrance Chemistry*, Academic Press, Inc. (1982), pp. 349–396.

*Helv. Chim. Acta* 20 (1937) p. 1474.

Muyaiyama et al. Chemical Abstracts, vol. 87, No. 5490r, 1977.

Ishihara et al, Chemical Abstracts, vol. 83, No. 78672d, 1975.

*Primary Examiner*—James H. Reamer
*Attorney, Agent, or Firm*—Pennie & Edmonds LLP

[57] ABSTRACT

The cycloaliphatic ketones of formula

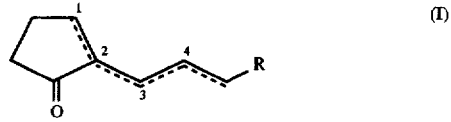
(I)

having two conjugated double bonds in positions 1 and 3, or 2 and 4, such as indicated by the dotted lines, and wherein R defines a $C_1$ to $C_3$ alkyl radical, useful intermediate products for the preparation of jasmonic derivatives, are prepared by an addition reaction btween the cyclopentanone and an aldehyde of formula

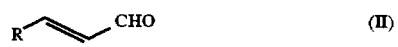
(II)

wherein the double bond is of (E) configuration and wherein R has the meaning indicated above, to provide a diene cyclopentanone of formula

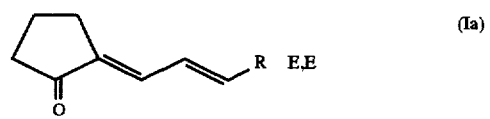
(Ia)

and, optionally, in that the cyclopentanone thus formed is subjected to a thermal treatment to provide a cyclopentenone of formula

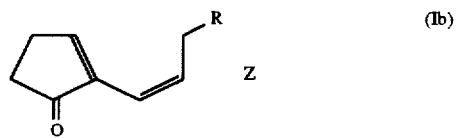
(Ib)

The 2-(E,2'Z)-but-2'-enylidene-cyclopentanone, 2-(1'Z)-but-1'-enyl-cyclopent-2-enone, 2-(E,2'E)-pent-2'-enylidene-cyclopentanone, 2-(Z,2'E)-pent-2'-enylidene-cyclopentanone and 2-(1'Z)-pent-1'-enyl-cyclopent-2-enone, as well as the malonic esters dimethyl [2-(pent-(1'Z)-enyl)-3-oxo-1-cyclopentyl]-malonate and dimethyl [2-(but-(1'Z)-enyl)-3-oxo-1-cyclopentyl]-malonate, are novel chemical entities.

7 Claims, No Drawings

PROCESS FOR THE MANUFACTURE OF UNSATURATED CYCLOALIPHATIC KETONES

TECHNICAL FIELD

The present invention relates to field of organic synthesis. It concerns, in particular, a process for the preparation of unsaturated cycloaliphatic ketones of formula

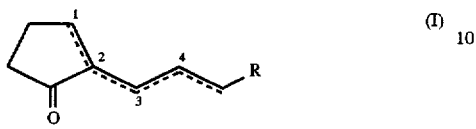
(I)

having two conjugated double bonds in positions 1 and 3, or 2 and 4, such as indicated by the dotted lines, and wherein R defines a $C_1$ to $C_3$ alkyl radical.

PRIOR ART

The compounds of formula (I) are useful as intermediates for the preparation of jasmonic derivatives having well appreciated odor properties and amongst which there can be cited more particularly methyl dihydrojasmonate (Hedione®, registered trademark of Firmenich SA). Since its discovery, this latter compound has been the object of a great number of syntheses [see Edouard P. Demole, in Fragrance Chemistry, Ed. E. Theimer, Academic Press, 1982] and the interest of the perfumers for this compound has increased these last few years, following the development of preparation methods which make it possible to obtain the preferred cis isomer.

The method employed for the industrial manufacture of methyl dihydrojasmonate is characterized by a first step which consists of the aldol condensation between pentanal and cyclopentanone [see U.S. Pat. No. 3,158,644 and Helv. Chim. Acta 20, 1474 (1937)], a reaction which leads to the formation of 2-pentylidenyl-cyclopentanone, which compound is then isomerized into 2-pentyl-cyclopent-2-enone. This latter compound, when added upon of dimethyl malonate and decarboxylated, leads to a mixture of methyl dihydrojasmonate consisting essentially of the cyclanic trans isomer.

On the other hand, cis-methyl dihydrojasmonate has been prepared according to the literature via hydrogenation of methyl 3-oxo-2-pentyl-cyclopent-2-ene-acetate in the presence of aluminum methoxide [DE-OS 2 162 820]. Other methods have been reported using an isomerizing distillation of the trans compound in the presence of a carbonate of an alkaline or alkaline-earth metal. The major inconvenient of such processes resides in the fact that they only allow the formation of the desired compound in the form of a mixture wherein the content in cis isomer does not generally go beyond 30%.

DESCRIPTION OF THE INVENTION

The present invention provides a novel solution to the problem of an industrial production, which is both straightforward and economical, of methyl dihydrojasmonate, in the form of the cis or trans isomer, as well as its lower homologue or nor-methyl dihydrojasmonate.

The process of invention is oriented towards the preparation of a diene cyclopentanone of formula (I), more particularly in its isomeric form of formula

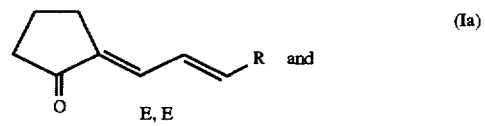

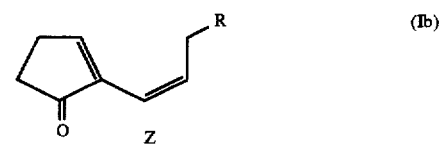

We observed that the aldol condensation in basic medium of an aldehyde of formula R—CH=CH—CHO, wherein the double bond has an (E) configuration, with the cyclopentanone gave rise to the formation of dienones (Ia) and not, as might have been expected, to that of the allylic carbinols of formula

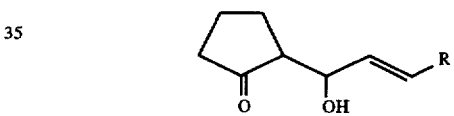

When the diene ketones (Ia), having an (E,E) type configuration, are subjected to thermal treatment at a temperature comprised between about 200° and 450° C., they convert into their isomers (Ib) having an endocyclic double bond and a (Z) configuration double bond in position 1 of the side chain. Now, it is precisely in this particular configuration that the compounds obtained by the process of the invention preferably react with dimethyl malonate for the subsequent step of the process for obtaining methyl dihydrojasmonate, or its lower homologue, following the reaction scheme hereafter:

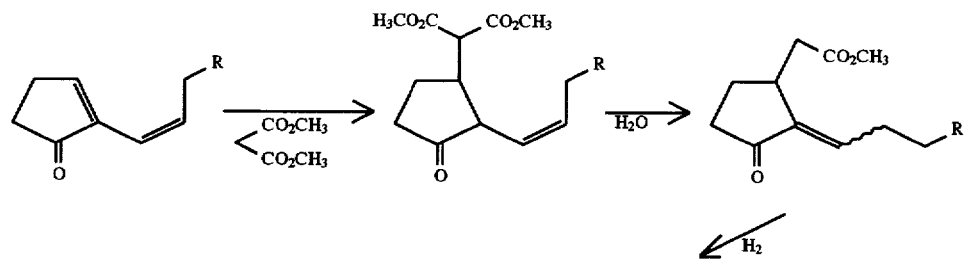

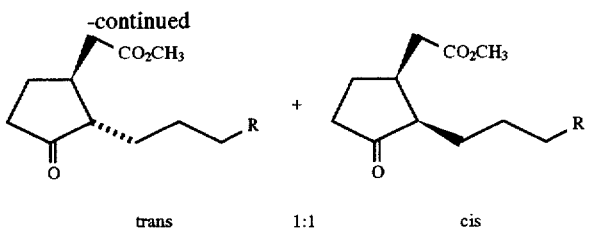

trans     1:1     cis

Both the addition of the dimethyl malonate and its decarboxylation take place according to methods analogous to those described in the literature [see U.S. Pat. No. 3,158,644 and DE-OS 2 162 820].

As regards the hydrogenation, it can be carried out in the presence of palladium on charcoal to provide an equimolar mixture of methyl dihydrojasmonate or nor-jasmonate, in their trans and cis isomeric forms.

One of the major advantages of the synthetic approach suggested by the present invention resides in the fact that, thanks to the cycloaliphatic ketones prepared by the process described, it is possible to prepare, through a judicious choice of the hydrogenation method, just as well the mixtures rich in cis isomer, as those containing essentially the trans isomer.

The present invention thus relates to a process for producing cycloaliphatic ketones of formula

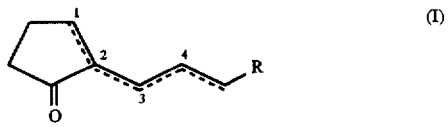

(I)

having two conjugated double bonds in positions 1 and 3, or 2 and 4, such as indicated by the dotted lines, and wherein R defines a $C_1$ to $C_3$ alkyl radical, said process being characterized in that there is added to the cyclopentanone, in the presence of a basic agent, an aldehyde of formula

(II)

wherein the double bond has an (E) configuration and R has the meaning indicated above, to provide a diene cyclopentanone of formula

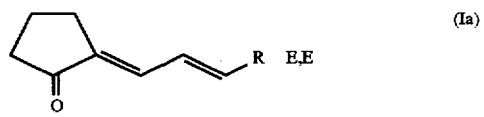

(Ia)

and, optionally, in that the thus formed cyclopentanone is subjected to a thermal treatment to give a cyclopentenone of formula

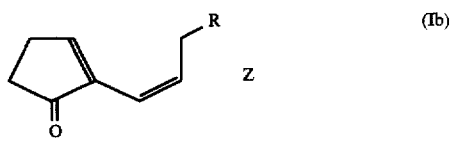

(Ib)

Amongst the compounds (Ia) and (Ib) thus obtained, there are some which are novel chemical entities. Such is the case of 2-E,2'Z)-but-2'-enylidene-cyclopentanone, of 2-(1'Z)-but-11'-enyl-cyclopent-2-enone, of 2-(E,2'E)-pent-2'-enylidene-cyclopentanone, of 2-(Z,2'E)-pent-2'-enylidene-cyclopentanone and of 2-(11 Z)-pent-1'-enyl-cyclopent-2-enone, which compunds are also the object of the invention.

The present invention also relates to the carboxylic diesters of formula

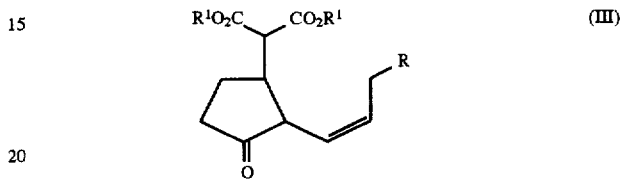

(III)

wherein R has the meaning indicated above in formula (I) and $R^1$ represents a lower alkyl. These are novel compounds obtained by means of methods similar to those known via addition of a dialkyl malonate onto a cyclopentanone of formula (Ib) in the presence of a basic agent such as an alkaline metal alkoxide.

As illustrated by way of the above-cited reaction scheme, diesters (III) are useful intermediates for the preparation of fragrant jasmonic derivatives.

According to the process of the invention, the addition of aldehyde (II) onto the cyclopentanone takes place in the presence of a basic agent. As the basic agent, there will be preferably used an alkali metal hydroxide or alkoxide, such as for example sodium hydroxide or methoxide. These are bases of current use for this type of reaction.

The following step, which consists of the isomerisation of the obtained diene cyclopentanones (Ia) essentially in the form of (E,E) configuration isomers into their (1'Z) configuration isomers (Ib), occurs via thermal treatment. The preferred temperature for such a treatment lies between about 200° and 450° C.

The reaction is carried out in a conventional oven or simply in a tube, preferably a quartz tube, heated to the chosen temperature and optionally swept by a flow of an inert gas, nitrogen or argon for example. The starting product is gradually introduced in one of the extremities of the tube, whereas at the other end the desired product is collected by condensation of the resulting vapors. Its purification can be carried out by one of the usual methods, such as column chromatography or fractional distillation.

The (E)-unsaturated aldehydes, used as starting products in the process for the preparation of the cycloaliphatic ketones (I) according to the invention, are commercial products of varied origin [see for example: Fluka AG, Buchs, Switzerland].

The invention is described in further detail by way of the following examples wherein the temperatures are indicated in degrees Celsius and the abbreviations have the usual meaning in the art.

EMBODIMENTS OF THE INVENTION

Example 1

2-(E,2'E)-Pent-2'-enylidene-cyclopentanone a. 180 ml of caustic soda 1M were added dropwise to 450 g (5.36 mole) of cyclopentanone maintained under stirring at about 5°–10°. The mixture becomes yellow through the addition. At this same temperature, there were then added during 1h to the reaction mixture 150 g (1.78 mole) of (E)-pent-2-enal. The reaction is exothermic and the color turns from yellow to brown. Stirring was maintained during a further 4h while the temperature was taken to about 20°. The mixture was extracted with ether (3×300 ml) and the organic extracts were washed with an aqueous solution of HCl, neutralized with NaHCO$_3$, water and then dried. By evaporation and distillation of the obtained residue (525 g), there were obtained 227 g of a fraction at B.p. 87°/0.5–0.7 hPa. The content in the desired diene ketone is 88% (yield 74%).

NMR ($^1$H, 360MHz, CDCl$_3$): 1.06(t, J=7.5 Hz, 3H); 1.96(txt, J=8 and 7.5 Hz, 2H); 2.23(qxd, J=7.5 and 6 Hz, 2H); 2.34(t, J=8 Hz, 2H); 2.69(t finely divided, J=7.5 Hz, 2H); 6.17(dxd, J=15 and 10.5 Hz, 1H); 6.24(txd, J=15 and 6 Hz, 1H); 6.92(d finely divided, J=10.5 Hz, 1H) 5 ppm NMR ($^{13}$C, 90.5 MHz, CDCl$_3$): 207.9(s); 147.4(d); 134.9 (s); 131.9(d); 125.9(d); 38.6(t); 27.1(t); 26.5(t); 19.9(t); 13.0(q) 6 ppm MS: 150(M+, 13); 135(2), 121(100), 107(2), 91(10), 79(25), 77(15), 65(5), 55(4), 39(8), 27(4).

2-(1'Z)-Pent-1'-enyl-cyclopent-2-enone b. 215 g (purity 88%) of 2-(E,2'E)-pent-2'-enylidene-cyclopentanone were introduced in a quartz column of 100×0.8 cm heated to 350° and swept by a nitrogen flow of 6 l/h. The introduction took place via a syringe at a rate of about 12–15 g/h. The resulting product is recovered at 20°.

The column was then rinsed with 30 ml of cyclohexane and the condensed liquid concentrated under vacuum to provide a 7:3 mixture of 2-(1'Z)-pent-1'-enyl-cyclopent-2-enone and of starting product. Distillation on residue provided 192 g of a mixture containing 60% of 2-(1'Z)-pent-1'-enyl-cyclopent-2-enone together with 23% of starting product, as well as a certain amount (12%) of two of its configuration isomers, i.e. a yield of 73%.

The obtained mixture can be used without purification in the following step. If desired, 2-(1'Z)-pent-1'-enyl-cyclopent-2-enone can be purified by fractional distillation or column chromatography.

The spectra data of a sample purified by chromatography on a silica column (Chromagel 35–70μ; 57 g) and a mixture of cyclohexane/ether 95:5 were as follows:

NMR ($^1$H, 360 MHz, CDCl$_3$): 0.94(t, J=7.5 Hz, 3H); 1.47(qxt, J=7.5 and 7.5 Hz, 2H); 2.19(txd finely divided, J=7.5 and 7 Hz, 2H); 2.40(m, 2H); 2.67(m, 2H); 5.80(txd, J=12 and 7 Hz, 1H); 6.04(d finely divided, J=12 Hz, 1H); 7.53(t, J=3 Hz, 1H) δ ppm NMR ($^{13}$C, 90.5 MHz, CDCl$_3$): 208.9(s); 158.0(d); 141.1(s); 136.9(d); 117.6(d); 33.9(t); 31.8(t); 26.9(t); 22.7 (t); 13.9(q) δ ppm MS: 150(M$^+$, 77); 135(34), 121(73), 117(17), 108(25), 91(54), 79(100), 77(62), 65(22), 55(24), 39(32), 27(19).

Example 2

Dimethyl [2-(pent-(1'Z)-enyl)-3-oxo-1-cyclopentyl]-malonate 37.5 g (purity 74%; 0.25 mole) of 2-(1'Z)-pent-1'-enyl-cyclopent-2-enone were added dropwise and under stirring at 5°–10° (2h) to a mixture of 33 g (0.25 mole) of methyl malonate, 80 ml of methanol and 1.7 g of sodium methoxide at 30% in methanol. Stirring was maintained for 4h at 5°–10° before acidification of the mixture by addition of 10 ml of acetic acid and concentrating under vacuum at 55°/200 hPa. The concentrated mixture is diluted in water and ether. The organic layer is washed with water (2×), dried over magnesium sulfate and concentrated by means of a rotating evaporator to provide 73 g of raw product. Via distillation, 32.2 g of the desired diester having B.p. 120°–145°/0.5 hPa (yield 45%) were obtained.

A sample for analysis was obtained by chromatography on a silica column (Chromagel 35–70 μ; 60 g); eluting agent: cyclohexane/ether 9:1 to 1:1.

Its analytical characteristics were the following:

NMR ($^1$H, 360 MHz, CDCl$_3$): 0.92(t, J=7.5 Hz, 3H); 1.40(qxt, J=7.5 and 7.5 Hz, 2H); 1.76(m, 1H); 2.00(m, 2H); 2.28(m, 2H); 2.45(m, 1H); 2.63(m, 1H); 3.10(dxd, J=11 and 10 Hz, 1H); 3.49(d, J=7 Hz, 1H); 3.70(s, 3H); 3.75(s, 3H); 5.03(dxd finely divided, J=11 and 10 Hz, 1H); 5.75(txd, J=11 and 7 Hz, 1H) 8 ppm NMR ($^3$C, 90.5 MHz, CDCl$_3$): 215.7(s); 168.6(s); 168.3 (s); 136.2(d); 124.1(d); 54.1(d); 52.6(d); 52.5(q); 52.4(q); 43.3(d); 37.4(t); 29.9(t); 24.9(t); 22.8(t); 13.9(q) δ ppm MS:282(M$^+$, 6); 264(1), 251(2), 233(1), 219(9), 205(1), 191(5), 177(3), 163(4), 151(95), 150(100), 133(93), 121 (46), 117(13), 109(28), 101(19), 93(37), 79(63), 67(27), 59(37), 55(32), 41(30), 27(21).

Example 3

2-(E,2'E)-But-2'-enylidene-cyclopentanone a. 200 ml of caustic soda 1M were added dropwise to 504 g (6 mole) of cyclopentanone maintained under stirring at about 20°. The mixture becomes yellow through the addition.

140 g (2 mole) of crotonaldehyde were then added dropwise at 5°–10° in 1 ½h and the color of the mixture turns to light brown, while stirring was maintained during a further 3h maintaining the temperature of the mixture at 20°. After extraction with ether (3×300 ml) the organic layer was separated and the combined ether extracts were washed with HCl (1N), neutralized with NaHCO$_3$, washed with an aqueous solution saturated with NaCl and then dried over MgSO$_4$.

By evaporating in a rotating evaporator under vacuum, there were obtained 562 g of concentrate which were then distilled to provide a fraction of 207 g at B.p. 56°–73°/0.6 hPa. Further distillation on a Widmer type column provided a fraction having B.p. 60°–62°/0.6 hPa of 179 g of the desired cyclopentanone having a purity of 88% (yield 58%).

Its analytical characters were as follows:

NMR ($^1$H, 360 MHz, CDCl$_3$): 1.89(d, J=5 Hz, 3H); 1.96(txt, J=8 and 7 Hz, 2H); 2.34(t, J=8 Hz, 2H); 2.68(t finely divided, J=7 Hz, 2H); 6.20(m, 2H); 6.90(d finely divided, J=8 Hz, 1H) δ ppm NMR ($^{13}$C, 90.5 MHz, CDCl$_3$): 207.8(s); 140.6(d); 134.7(s); 131.6(d); 128.3(d); 38.6(t); 27.0(t); 19.9(t); 19.1(q) δ ppm MS: 136(M$^+$, 29); 121(100), 107(3), 103(1), 91(12), 79(59), 74(1), 65(10), 55(4), 51(10), 39(19), 27(10)

Amongst the secondary compounds there was 2-(E,2'Z)-but-2'-enylidene-cyclopentanone, the analytical characteristics of which were the following:

NMR ('H, 360 MHz, CDCl$_3$): 1.90(d, J=8 Hz, 3H); 1.96(m, 2H); 2.36(t, J=8 Hz, 2H); 2.68(t finely divided, J=6 Hz, 2H); 6.11(m, 2H); 7.27(d finely divided, J=12 Hz, 1H) δ ppm NMR (13C, 90.5 MHz, CDCl$_3$): 208.0(s); 137.1(d); 136.5 (s); 126.0(d); 125.8(d); 38.7(t); 26.9(t); 19.8(t); 14.1(q) δ ppm MS: 136(M+, 29); 121(100), 107(4), 103(1), 91(11), 79(45), 65(5), 51(3), 39(4), 27(1) as well as 2-(Z,2'E)-but-2'-enylidene-cyclopentanone:

NMR ($^1$H, 360 MHz, CDCl$_3$): 1.85(d finely divided, J=8 Hz, 3H); 1.90(txt, J=8 and (8 Hz, 2H); 2.34(t, J=8 Hz, 2H); 2.63(t, J=8 Hz, 2H); 5.99(dxq, J=8 and J=16 Hz, 1H); 6.33(d, J=12 Hz, 1H); 7.53(dxd finely divided, J=8, 12 and 16 Hz, 1H) δ ppm NMR ($^{13}$C, 90.5 MHz, CDCl$_3$): 207.8(s); 139.0(d); 136.3 (d); 132.4(s); 128.0(d); 40.6(t); 31.8(t); 20.5(t); 18.6(q) δ ppm MS: 136(M$^+$, 19); 121(100), 107(3), 103(1), 91(10), 79(29), 65(4), 51(3), 39(3), 27(1)

b. 2-(1'Z)-but-1'-enyl-cyclopent-2-enone 85 g (purity 88%) of 2-(E,2'E)-but-2'-enylidene-cyclopentanone were introduced into a quartz column, of 100 cm of length and 0.8 cm of diameter, heated at 350° and swept by a nitrogen flow of 6 l/h.

The introduction rate was of 12–15 g/h. The product was recovered at 200. The condensate presents itself in the form of a 7:3 mixture of 2-(1'Z)-but-1'-enyl-cyclopent-2-enone and starting product.

The quartz column was rinsed with 30 ml of cyclohexane and the condensate was concentrated under vacuum. By repeated distillation on a Widmer column, there were obtained 58 g of the desired ketone having a purity of 68%. B.p. 84°–86°/4 hPa.

The product was purified by distillation.

The analytical characters of the product obtained were the following:

NMR ($^1$H, 360 MHz, CDCl$_3$): 1.05(t, J=7.5 Hz, 3H); 2.23(qxd finely divided, J=7.5 and 7 Hz, 2H); 2.41(m, 2H); 2.68(m, 2H); 5.78(txd, J=12 and 5 Hz, 1H); 6.00(d finely divided, J=12 Hz, 1H); 7.52(t, J=3 Hz, 1H) δ ppm NMR ($^3$C, 90.5 MHz, CDCl$_3$): 209.0(s); 158.2(d); 141.0 (s); 138.6(d); 117.0(d); 33.9(t); 26.9(t); 23.0(t); 13.9(q) δ ppm MS: 136(M$^+$, 99), 121(74), 117(15), 107(23), 103(10), 91(54), 79(100), 77(70), 74(3), 65(27), 55(18), 51(23), 39(44), 27(19).

Example 4

Dimethyl [2-but-(1'Z)-enyl)-3-oxo-1 -cyclopentyl]-malonate 32 g (0.24 mole) of 2-(1'Z)-but-1'-enyl-cyclopent-2-enone (purity 71%) were added dropwise under stirring at 5°–10° in 75 min to a mixture of 31 g (0.24 mole) of dimethyl malonate in 80 ml of methanol and 1.7 g of sodium methoxide at 30% in methanol. Stirring was continued for 4 h at 5°–10°.

The reaction mixture was acidified by addition of 10 ml of acetic acid before being concentrated by means of a rotating evaporator at 55°/200 hPa. The obtained concentrate was diluted in water and ether and then the organic layer was washed with water (2×), dried over MgSO$_4$ and concentrated to provide 68 g of residue. Distillation of this product yielded the desired malonic ester at B.p. 130°/0.5 hPa. An analytical sample was purified by redistillation.

Its analytical characters were the following:

NMR ($^1$H, 360 MHz, CDCl$_3$): 0.99(t, J=7.5 Hz, 3H); 1.75(m, 1H); 2.05(m, 2H); 2.27(m, 2H); 2.43(m, 1H); 2.63 (m, 1H); 3.09(dxd, J=11 and 10 Hz, 1H); 3.49(d, J=7 Hz, 1H); 3.70(s, 3H); 3.75(s, 3H); 4.99(dxd finely divided, J=11 and 10 Hz, 1H); 5.73(txd, J=11 and 7 Hz, 1H) δ ppm NMR ($^{13}$C, 90.5 MHz, CDCl$_3$): 215.7(s); 168.6(s); 168.3 (s); 137.8(d); 123.5(d); 54.2(d); 52.6(d); 52.5(q); 52.4(q); 43.2(d); 37.4(t); 25.0(t); 21.1(t); 14.2(q) δ ppm MS: 268(M$^+$, 3); 237(1), 219(2), 205(10), 193(2), 187(2), 177(5), 163(3), 149(5), 137(100), 136(78), 133(46), 121 (17), 107(8), 101(9), 93(20), 79(20), 69(10), 59(16), 55(8), 41(5), 29(4).

Example 5

Proceeding as indicated in the preceding examples, but reacting hex-2-enal onto cyclopentanone, there was obtained 2-(E,2'E)-hex-2'-enylidene-cyclopentanone, the analytical characteristics of which were as follows:

NMR ($^1$H, 360 MHz, CDCl$_3$): 0.93(t, J=7.5 Hz, 3H); 1.46(qxt, J=7.5 and 7.5 Hz, 2H); 1.96(txt, J=8 and 8 Hz, 2H); 2.18(txd, J=7.5 and 7 Hz); 2.34(t, J=8 Hz); 2.68(t finely divided, J=8 Hz, 2H); 6.18(m, 2H); 6.90(d finely divided, J=8 Hz, 1H) δ ppm NMR ($^{13}$C, 90.5 MHz, CDCl$_3$): 207.9(s); 145.9(d); 134.8 (s); 131.9(d); 127.0(d); 38.6(t); 35.5(t); 27.0(t); 22.1(t); 19.9(t); 13.7(q) δ ppm MS: 164(M$^+$, 10); 149(1), 135(3), 121(100), 107(3), 91(13), 79(19), 77(21), 65(7), 55(5), 51(5), 39(12), 27(11)

The compound thus obtained was treated as indicated in Example 3.b to provide 2-(1 'Z)-hex-1'-ethyl-cyclopent-2-enone:

NMR ($^1$H, 360 MHz, CDCl$_3$): 0.91(t, J=7.5 Hz, 3H); 1.35(m, 2H); 1.42(m, 2H); 2.23(txd finely divided, J=7.5 and 7 Hz, 2H); 2.43(m, 2H); 2.68(m, 2H); 5.81(txd, J=12 and 7 Hz, 1H); 6.03(d finely divided, J=12 Hz, 1H); 7.53(t, J=3 Hz, 1H) δ ppm NMR ($^{13}$C, 90.5 MHz, CDCl$_3$): 209.0(s); 158.0(d); 141.1 (s); 137.2(d); 117.4(d); 33.9(t); 31.6(t); 29.4(t); 26.9(t); 22.4(t); 13.9(q) δ ppm MS: 164(M$^+$, 60); 149(9), 135(42), 121(68), 117(15), 108(32), 96(34), 91(59), 79(100), 77(65), 65(24), 55(19), 39(40), 27(28)

Finally, the conversion of this compound into dimethyl [2-hex-(1'Z)-enyl)-3-oxo-1-cyclopentyl]- malonate is obtained according to Example 4.

Its NMR spectrum was the following:

NMR ($^1$H, 360MHz, CDCl$_3$): 0.90(t, J=7.5Hz, 3H); 1.34 (m, 4H); 1.75(m, 1H); 2.03(m, 2H); 2.27(m, 2H); 2.44(m, 1H); 2.64(m, 1H); 3.10(dxd, J=11 and 10 Hz, 1H) δ ppm

We claim:

1. Process for the preparation of cycloaliphatic ketones of formula

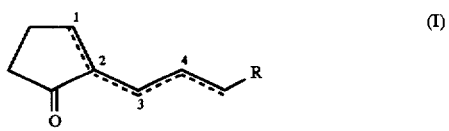

having two conjugated double bonds in positions 1 and 3, or 2 and 4, such as indicated by the dotted lines, and wherein R defines a C$_1$ to C$_3$ alkyl radical, said process being characterized in that there is added to the cyclopentanone, in the presence of a basic agent, an aldehyde of formula

wherein the double bond is of (E) configuration and wherein R has the meaning indicated above, to provide a diene cyclopentanone of formula

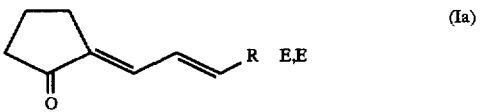

and, optionally, in that the cyclopentanone thus formed is subjected to a thermal treatment to provide a cyclopentenone of formula

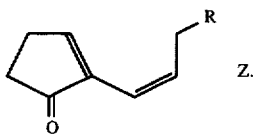

(Ib)

2. Process according to claim 1, characterized in that the diene cyclopentanone of formula (Ia)E,E is subjected to a thermal treatment at a temperature of from about 200° to about 450° C. to provide a cyclopentenone of formula I(b)Z.

3. Compounds of formula (Ia) and (Ib) such as defined in claim 1, selected from the following group:
   2-(1'Z)-but-1'-enyl-cyclopent-2-enone,
   2-(E,2'E)-hex-2'-enylidene-cyclopentanone,
   2-(E,2'E)-pent-2'-enylidene-cyclopentanone and
   2-(1'Z)-pent-1'-enyl-cyclopent-2-enone.

4. Carboxylic diesters of formula

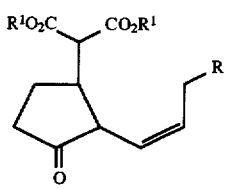

(III)

wherein R represents a $C_1$ to $C_3$ alkyl radical and $R^1$ defines a lower alkyl.

5. A carboxylic diester according to claim 4, specifically as
   dimethyl [2-(pent-1'Z)-enyl)-3-oxo-1-cyclopentyl]-malonate,
   dimethyl [2-(but-1'Z)-enyl)-3-oxo-1-cyclopentyl]-malonate, and
   dimethyl [2-(hex-1'Z)-enyl)-3-oxo-1-cyclopentyl]-malonate.

6. A method for making the carboxylic diesters of formula

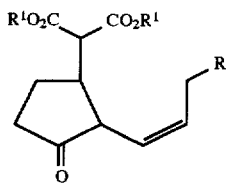

(III)

wherein R represents a $C_1$ to $C_3$ alkyl radical and $R^1$ defines a lower alkyl, which comprises subjecting the cyclopentenone of formula (Ib)Z according to claim 2 to an addition reaction with a dialkyl malonate.

7. A method for making the cis and trans dihydrojasmonates of formula

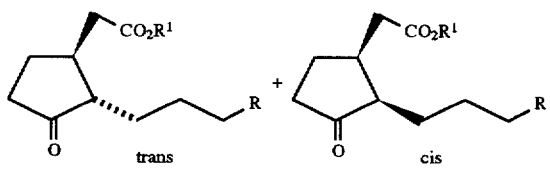

wherein R represents a $C_1$ to $C_3$ alkyl radical and $R^1$ defines a lower alkyl, which comprises decarboxylating the carboxylic diesters of formula III according to claim 6, and hydrogenating the decarboxylation product to produce the cis and trans dihydrojasmonates wherein the ratio of cis to trans isomers is 1:1.

* * * * *